United States Patent [19]

Bardy

[11] Patent Number: 5,099,838

[45] Date of Patent: * Mar. 31, 1992

[54] ENDOCARDIAL DEFIBRILLATION ELECTRODE SYSTEM

[75] Inventor: Gust H. Bardy, Seattle, Wash.

[73] Assignee: Medtronic, Inc., Minneapolis, Minn.

[*] Notice: The portion of the term of this patent subsequent to May 14, 2008 has been disclaimed.

[21] Appl. No.: 284,955

[22] Filed: Dec. 15, 1988

[51] Int. Cl.$^5$ ............................................. A61N 1/39
[52] U.S. Cl. .................................. 128/419 D; 128/786
[58] Field of Search .................. 128/419 D, 421, 783, 128/784, 785, 786

[56] References Cited

U.S. PATENT DOCUMENTS

| | | | |
|---|---|---|---|
| Re. 27,652 | 5/1973 | Mirowski et al. | 128/419 D |
| 3,942,536 | 3/1976 | Mirowski et al. | 128/419 D |
| 4,161,952 | 7/1979 | Kinney et al. | 128/786 |
| 4,458,677 | 7/1984 | McCorkle, Jr. | 128/786 |
| 4,481,953 | 11/1984 | Gold et al. | 128/786 |
| 4,548,203 | 10/1985 | Tacker, Jr. et al. | 128/419 D |
| 4,641,656 | 2/1987 | Smits | 128/419 D |
| 4,662,377 | 5/1987 | Heilman et al. | 128/419 D |
| 4,708,145 | 11/1987 | Tacker, Jr. et al. | 128/419 D |
| 4,727,877 | 3/1988 | Kallok | 128/419 D |

FOREIGN PATENT DOCUMENTS 0281219 1/1988 European Pat. Off. .

OTHER PUBLICATIONS

Ewy et al., "Electrode System for Permanent Implantable Defibrillators," Medical Instrumentation, vol. 12, No. 5, 10-1978.

Primary Examiner—William E. Kamm
Assistant Examiner—Kennedy J. Schaetzle

[57] ABSTRACT

An endocardial defibrillation electrode system as provided, including a coronary sinus lead, a ventricular lead, and a subcutaneous plate. The coronary sinus lead includes an elongated electrode adapted for location in the coronary sinus, extending into the great vein, and terminating in the vicinity of the left atrial appendage. The right ventricular electrode may be located either in the right ventricular apex, or may extend from the right ventricular apex to the vicinity of the tricuspid valve. This subcutaneous electrode preferably is a large surface electrode, adapted for implant in the vicinity of the heart. A variety of defibrillation pulse regimes are disclosed, optimized for use with the defibrillation electrode system, and with subgroupings of the disclosed electrodes.

3 Claims, 6 Drawing Sheets

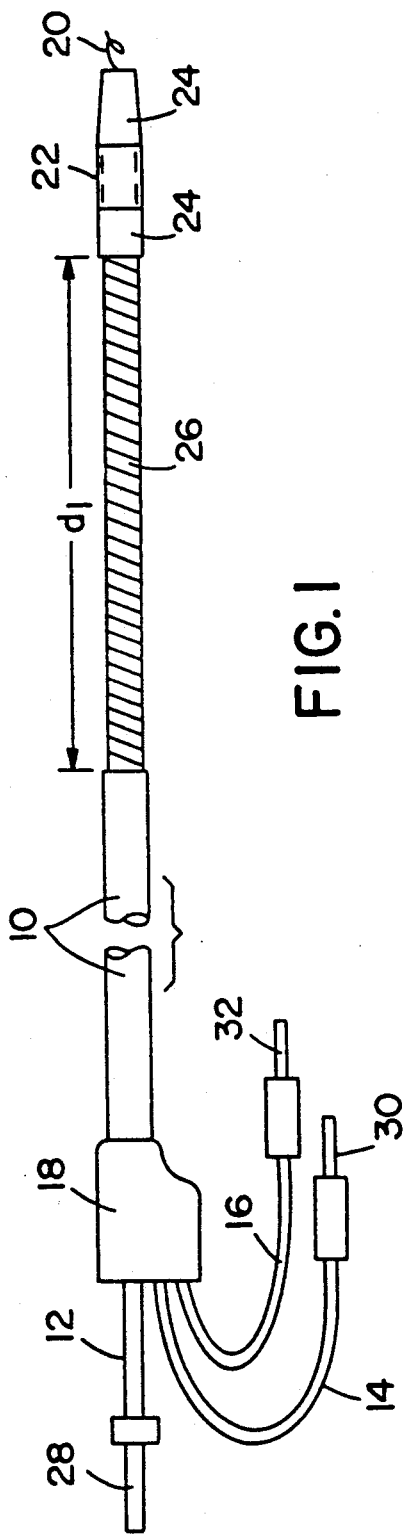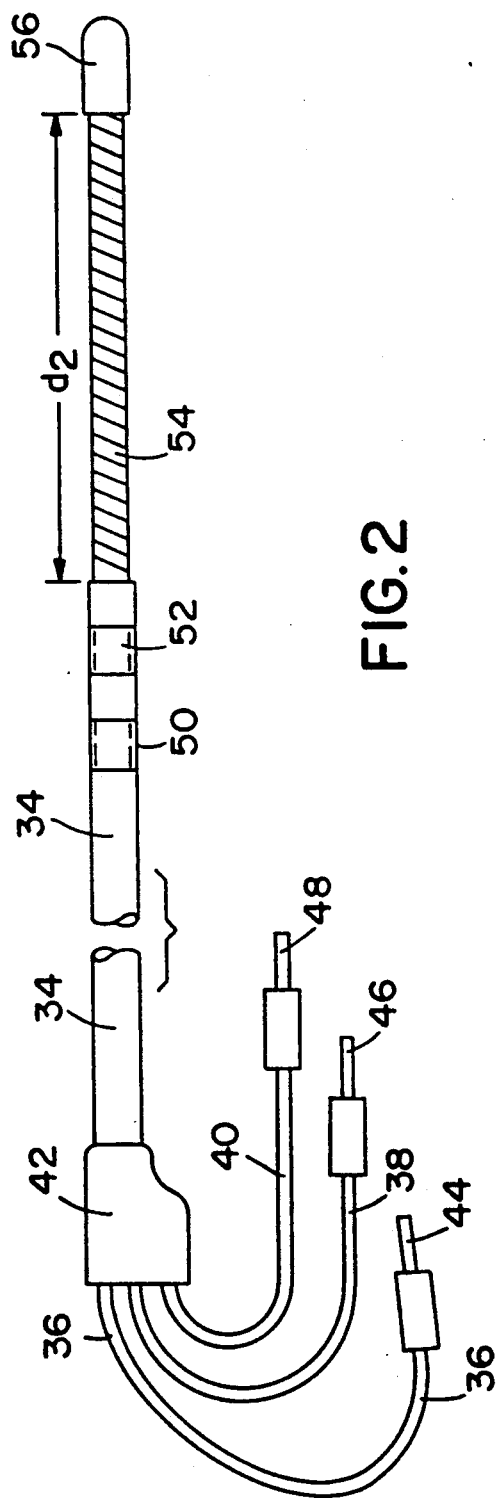

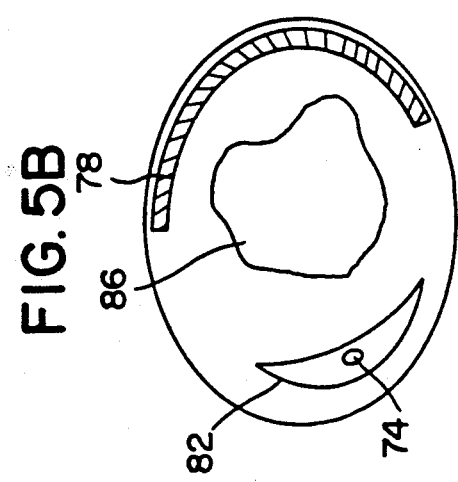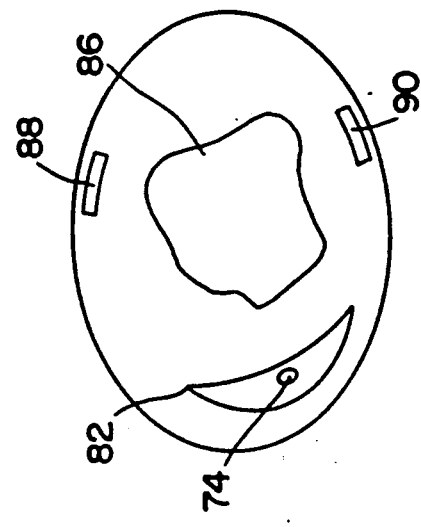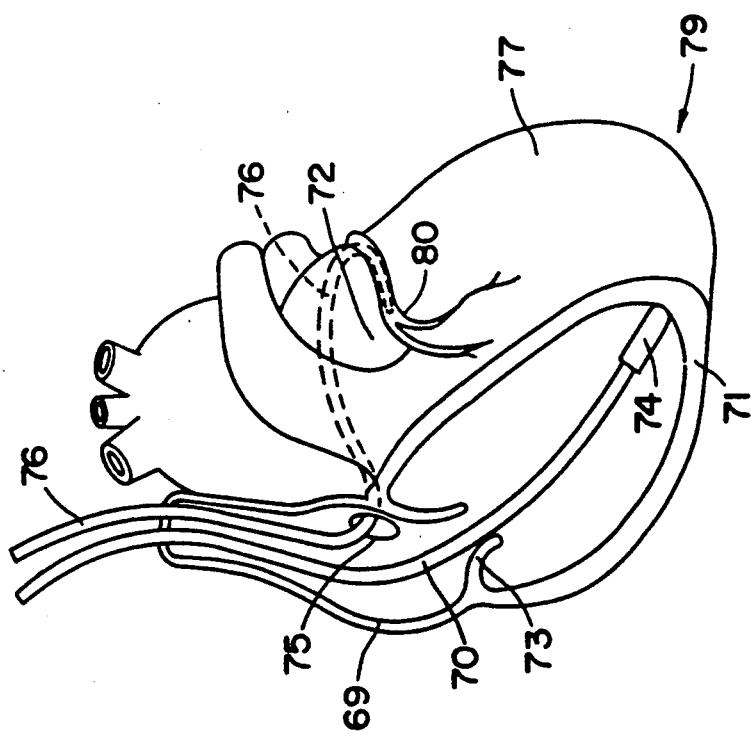

ENDOCARDIAL DEFIBRILLATION ELECTRODE SYSTEM

RELATED APPLICATIONS

Reference is made to commonly assigned co-pending application Ser. No. 003,358, by Rahul Mehra, filed Jan. 14, 1987, for a METHOD OF DEFIBRILLATING A HEART, incorporated herein by reference in its entirety.

BACKGROUND OF THE INVENTION

This invention relates to implantable stimulators generally, and to implantable defibrillators more particularly.

Over the past twenty years, there has been substantial work toward developing a practical, implantable defibrillator. However, several significant problems must still be overcome. Early conceptions of implantable defibrillators, such as disclosed in U.S. Pat. No. Re. 27,652, by Mirowski et al, envision a system employing a ventricular endocardial electrode and a plate electrode mounted to the heart directly, subcutaneously, or to the skin. However, it was recognized early on that a totally transvenous system would be desirable in order to simplify the use of implantable defibrillators. One such system is suggested in U.S. Pat. No. 3,942,536 by Mirowski et al, which discloses a transvenous lead having electrodes intended for location in the right ventricular apex and superior vena cava. Such systems were eventually tested in human beings, with some success. However, currently available commercial versions of implantable defibrillators employ epicardial patch electrodes in conjunction with transvenous electrodes.

While systems employing a transvenous endocardial electrode in combination with an epicardial patch electrode are workable, a thoracotomy is required in order to apply the epicardial electrode. It is generally believed that it would be highly desirable to produce an implantable defibrillator system which would entirely avoid the necessity of a thoracotomy, and there has been substantial work directed towards such systems, as disclosed in U.S. Pat. No. 4,727,877 issued to Kallok, and U.S. Pat. No. 4,708,145 issued to Tacker et al. Both the Tacker et al and Kallok patents disclose the use of a transvenous, two electrode lead in combination with a subcutaneous patch electrode.

Transvenous ventricular defibrillation electrodes are shown in the above-cited Mirowski patents and in the Tacker and Kallok patents cited above. Other endocardial defibrillation electrodes are disclosed in U.S. Pat. No. 4,481,953 issued to Gold et al, U.S. Pat. No. 4,161,952 issued to Kinney et al and U.S. Pat. No. 4,641,656 issued to Smits. The Kinney, Smits and Kallok patents also disclose transvenous defibrillation electrodes intended for use in or adjacent to the coronary sinus.

SUMMARY OF THE INVENTION

The present invention is directed toward defibrillation lead systems and methods of their use which allow for the use of an implantable defibrillator without the necessity of a thoracotomy. In some embodiments, the electrode system includes a coronary sinus electrode, which extends from an area adjacent the opening of the coronary sinus and terminates in the great vein. This electrode is used in combination with subcutaneous plate electrodes and with right ventricular electrodes.

In some embodiments, an asymmetric biphasic pulse is employed in order to increase efficiency of delivery of electrical energy to the lead system and to facilitate construction of the defibrillator pulse generation circuitry. This waveform is discussed in more detail in U.S. patent application Ser. No. 003,358, by Rahul Mehra, filed Jan. 14, 1987, for a METHOD OF DEFIBRILLATING A HEART, cited above.

In some embodiments, single pulses are delivered between two or more electrodes. In other embodiments, sequential pulses are delivered between individual pairs of electrodes. All of the embodiments are directed toward the goal of providing a practical defibrillation lead system and pulse regime which eliminates the need for epicardial electrodes.

BRIEF DESCRIPTION OF THE DRAWINGS

FIG. 1 is a plan view of a ventricular defibrillation lead.

FIG. 2 is a plan view of a coronary sinus defibrillation lead.

FIGS. 5A, 5B and 5C illustrate a first embodiment of an all transvenous defibrillation lead system, employing the electrodes of FIGS. 1, 2 and 3.

DETAILED DESCRIPTION OF THE DRAWINGS

Figure 3:
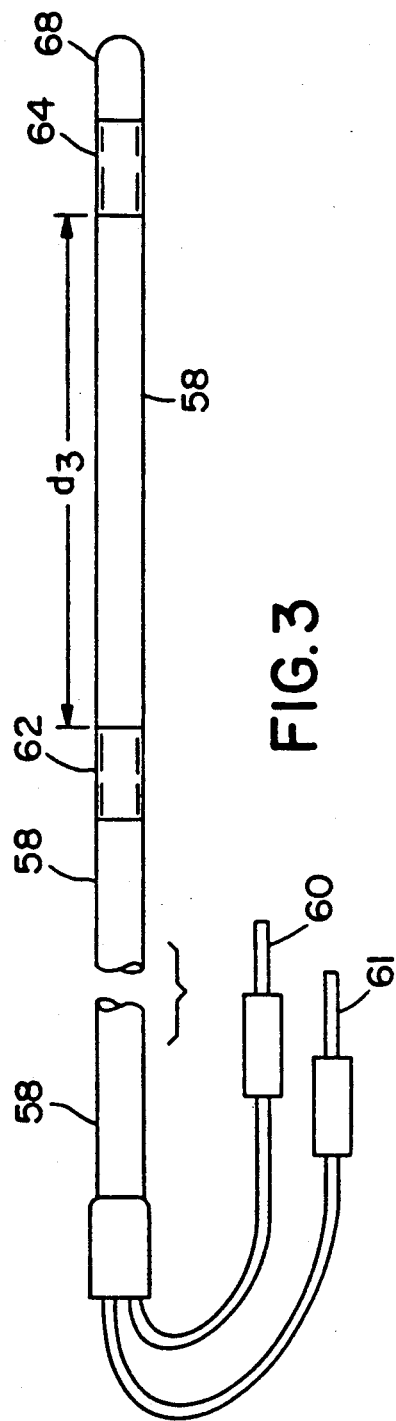
FIG. 3 is a plan view of an alternative embodiment of a coronary sinus defibrillation lead.

FIG. 1 shows a plan view of a defibrillation lead intended for use in the right ventricle of the human heart. The elongated, insulative lead body 10 contains three mutually insulated electrical conductors. The first, second and third mutually insulated electrical conductors 12, 14 and 16 all exit the lead body 10 at an insulative molding 18. Conductor 12 extends through the lead body to its distal tip, and is coupled to a helical electrode 20. Rotation of conductor 12 causes electrode 20 to rotate out of the tip of the lead and into the myocardium of the heart, in order to secure the lead within the ventricle. The operation of helical electrode 20 can be more completely understood by reference to U.S. Pat. No. 4,106,512 for a TRANSVENOUSLY IMPLANTABLE LEAD, by Bisping, issued Aug. 15, 1978, and incorporated herein by reference in its entirety.

The second conductor 14 is coupled to a ring electrode 22, mounted to the electrode head 24, which is otherwise insulative. This allows the combination of coil electrode 20 and ring electrode 22 to be used for both sensing the electrical signals in the heart indicative of contraction of the ventricle and for pacing the heart, as in a conventional cardiac pacemaker.

Third conductor 16 is coupled to an elongated coil electrode 26, which takes the form of a space wound coil, wrapped around the insulative lead body 10. Coil electrode 26 extends for a distance $D_1$, along the length of the lead body. $D_1$ is selected such that the proximal end of electrode 26 will terminate in the vicinity of the tricuspid valve when the coil electrode 20 is embedded in the myocardium of the right ventricular apex. Although different electrode sizes may be required for patients having differing heart sizes, it is generally expected that distance $d_1$ will be from approximately 4 cm to approximately 8 cm.

Conductors 12, 14 and 16 are each provided with an electrical connector pin 28, 30 and 32, respectively, to allow coupling of the lead to an implanted defibrillator or a defibrillator/pulse generator. Connector pin 28 also provides a convenient location to apply rotational force to conductor 12. Although the lead as illustrated employs separate connector pins for each conductor, an in-line connector assembly may also be employed.

FIG. 2 illustrates a coronary sinus lead. The lead is provided with an elongated insulative lead body 34, which contains three, mutually insulated conductors 36, 38 and 40. Conductors 36, 38 and 40 exit the proximal end of lead body 34 at insulative molding 42. Each of conductors 36, 38 and 40 is provided with a connector pin 44, 46 and 48, respectively.

Conductors 36 and 38 are coupled to ring electrodes 50 and 52, respectively. Electrodes 50 and 52 are mounted around the exterior of insulative lead body 34. In use, electrodes 50 and 52 are located in the right atrium, and may be located adjacent the opening of the coronary sinus or adjacent the entry point of the superior vena cava. Electrodes 50 and 52 allow for sensing of electrical signals indicative of contraction of the atrium, and may allow for stimulation of the atrium, employing a conventional pacemaker. The inclusion of electrodes 50 and 52 is believed especially desirable in circumstances in which dual chamber pacing, such as DDD pacing, DDI, or VDD pacing is desired in conjunction with defibrillation.

Conductor 40 is coupled to an elongated coil electrode 54, which takes the form of a space wound coil mounted to the exterior of insulative lead body 34. In use, it is intended that electrode 54 will extend from a point adjacent the opening of the coronary sinus and terminate distally in the great coronary vein. Preferably, electrode 54 will terminate within the great vein before it turns downward toward the base of the heart, in the vicinity of the left atrial appendage. This allows the electrode 54 to encircle a large percentage of the left ventricle, and is believed to provide substantially improved current distribution. The distal tip 56 of the lead is also insulative, and its tapered end is intended to facilitate passage of the lead into the coronary sinus and through the great vein. In order to allow the electrode to extend its full length into the great vein, the diameter of the lead in the area of the electrode and distal thereto is preferably 2.3 mm (7 F) or less and the length $d_2$ of electrode 54 is preferably 4 to 7 cm, although in enlarged hearts, an electrode length of 8 cm may be desirable.

The combination of the leads disclosed in FIG. 1 and FIG. 2 provides an extraordinarily flexible lead system, appropriate for use in implantable defibrillators, as well as in conjunction with single and dual chamber cardiac pacemakers. By using these two electrodes in combination, a lead system is provided that will allow for use of virtually any implantable defibrillator or pacemaker. The lead of FIG. 2 is especially beneficial in this regard, as electrode 54, when located in the coronary sinus great vein, stabilizes the locations of electrodes 50 and 52, allowing for reliable atrial sensing without the necessity of either an active fixation device or a preformed J-shaped configuration.

The preferred embodiment of the lead of FIG. 2 employs ring electrodes spaced 4–8 cm from the end of electrode 54. In this embodiment, the ring electrodes would lie adjacent the point of entry of the superior vena cava. This configuration may be superior if atrial stimulation is desired.

FIG. 3 illustrates an alternative coronary sinus lead for use in lead systems and methods as discussed below. The lead is provided with an elongated insulative lead body 58 which contains two conductors, each extending from one of connector pins 60 and 61 to one of ring electrodes 62 and 64. The tip 68 of the lead is insulative and rounded, facilitating its passage through the coronary sinus and great vein. Electrodes 62 and 64 are spaced apart in sufficient distance, $d_3$, such that when inserted into the coronary sinus and great vein, the electrode 62 in the general vicinity of the opening to the coronary sinus, electrode 64 is located in the great vein. Typically, $d_3$ will be from about 4 cm to about 6 cm, but larger spacing may be appropriate for enlarged hearts. The lead of FIG. 3 may be used in place of the lead of FIG. 2 in the defibrillation systems illustrated and discussed below.

Figure 4:
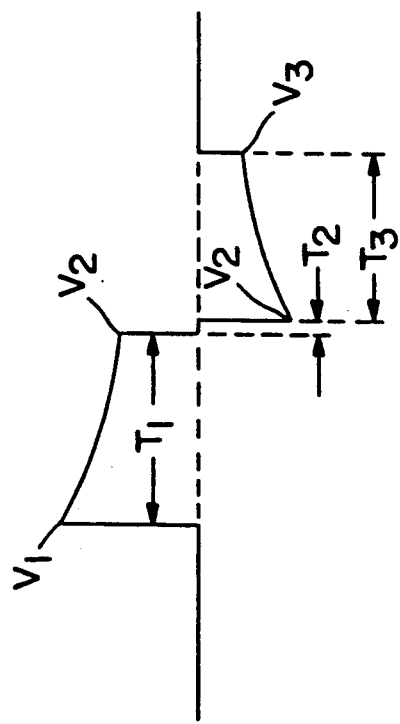
FIG. 4 shows an asymmetric, biphasic waveform useful in delivery of defibrillation pulses.

FIG. 4 illustrates a biphasic, asymmetric defibrillation pulse waveform believed to be particularly desirable for use in conjunction with defibrillation lead systems illustrated and discussed below. This waveform is discussed and described in more detail in the above cited U.S. patent application by Rahul Mehra. In contrast to previously known biphasic defibrillation waveforms, this waveform may be generated by the discharge of a single capacitor, rather than requiring a multiple capacitor system.

The waveform of FIG. 4 can be best be understood as the capacitive discharge waveform in which the polarity of the electrodes coupled to the capacitor is switched during delivery of the pulse. FIG. 4 illustrates the voltage waveform, as measured across the electrodes to which the capacitor is coupled. On initial connection of the output capacitor to the defibrillation electrodes, the stored voltage of the capacitor $V_1$ begins to decay. Over a period of time $T_1$, the voltage decays to a second voltage $V_2$. At this point, the polarity of the electrodes connected to the output capacitor is reversed, over a short time period $T_2$. The capacitor continues to discharge from voltage $V_2$ to a third voltage $V_3$, over a time period $T_3$, after which discharge of the capacitor is terminated. It has been found that the asymmetric biphasic waveform illustrated in FIG. 4 is efficacious of defibrillation, and simplifies construction of the defibrillation pulse generator. The ability to employ a single output capacitor to generate a biphasic output pulse is particularly beneficial in the context of an implantable defibrillator, in which size constraints are paramount, and in which the output capacitors typically occupy a substantial percentage of the device's volume.

Experimental work involving the waveform of FIG. 4 has generally employed tilts of 50–65 percent, and time periods $T_1$ and $T_3$ that are approximately equal and in the vicinity of 4 to 15 ms each. Initial voltages $V$ vary with the particular electrode systems employed.

FIG. 5A shows a cutaway view of the human heart in which the electrode leads have been mounted in their expected positions of use to provide a completely endocardial, transvenous defibrillation lead system. Ventricular lead 70 may take the form of the lead illustrated in FIG. 1. Alternatively, it may be a defibrillation lead of the type employing one or more cylindrical electrodes adjacent its distal end, as illustrated in U.S. Pat. No. 4,355,646, issued to Kallok et al. This patent is included herein by reference in its entirety. In this view, it can be seen that the ventricular lead 70 passes through the atrium 69, and is secured in the apex of the right ventricle 71. Defibrillation lead 70 includes at least one electrode surface 74 generally adjacent the distal end of lead 70, and located within the right ventricle 71 near its apex. The coronary sinus lead 76 (illustrated in FIG. 2) is shown passing through the superior vena cava, into the opening of the coronary sinus 75, through the great vein 80, and extending around the base of the left ventricle 77. When so mounted, the elongated defibrillation electrode 78 extends from a point adjacent the opening of the coronary sinus 75 and into the great vein 80. This provides a large surface area defibrillation electrode which is generally well spaced from the ventricular defibrillation electrode 74 and provides good current distribution in the area of the left ventricle 77. It is desirable to extend the electrode 78 around the heart as far as possible. However, it is important not to extend the electrode 78 downward through the great vein 80 toward the apex 79 of the heart, as this will bring the coronary sinus and right ventricular electrodes into close proximity to one another, interfering with proper current distribution. Generally, the distal end of the electrode 78 should be roughly adjacent the left atrial appendage 22.

The electrode system illustrated in FIG. 5A provides a completely transvenous defibrillation electrode system, which includes a larger percentage of the tissue of the left ventricle between its electrodes than prior art totally transvenous electrode systems employing superior vena cava and right ventricular electrodes. The biphasic waveform illustrated in FIG. 4 is also useful in conjunction with an electrode system as illustrated in FIG. 5A.

FIG. 5B shows a stylized cross-section of the heart, intended to illustrate the relative locations of the ventricular and coronary sinus electrodes. In this view, it can be seen that the right ventricular electrode 74 (visible in cross-section) is located within the right ventricular cavity 82, while the coronary sinus electrode 78 encircles the left ventricular cavity 86. In this view, it can be seen that a substantial percentage of the tissue of the left ventricle is located between electrode 74 and electrode 78, which provides for improved current distribution.

FIG. 5C shows a second stylized cross-section of the heart, illustrating the relative locations of right ventricular and coronary sinus/great vein electrodes. When a system comprising the leads of FIG. 1 and FIG. 3 is employed, the ventricular electrode 74 is again located in the right ventricular cavity 82. The proximal and distal electrodes 88 and 90 (corresponding to electrodes 62 and 64 in FIG. 3) are both located across the left ventricular cavity 86 from ventricular electrode 74.

The electrode system comprising the leads of FIG. 1 and FIG. 3 provides extraordinary flexibility in the choice of pulse delivery regimes. For example, electrodes 88 and 90 may be electrically coupled to one another, and a pulse delivered between them in electrode 82, approximating the delivery system illustrated in FIG. 5B. Alternatively, two of the electrodes, for example 82 and 88, may be used to deliver a first pulse, with a second pulse delivered between electrodes 82 and 90. As another alternative, the peripheral rotating pulse regime disclosed in the above cited Smits patent may be used employing these electrodes. In this regime, two of the electrodes, for example 82 and 88, are coupled to one another, and first pulse delivered between these electrodes and electrode 90. Following this, electrodes 82 and 90 may be paired, and a second pulse delivered between these pair electrodes and electrode 88. This pulse regime is discussed in more detail in U.S. Pat. No. 4,641,656 for a "Cardioversion and Defibrillation Lead Method", issued Feb. 10, 1987 to Smits. This patent is incorporated herein by reference in its entirety.

As a result, the electrode system illustrated in FIG. 5C is believed to be especially beneficial, as it provides an electrode system appropriate for use with single pulse, simultaneous pulse, sequential pulse, and peripheral rotating pulse regimes. In conjunction with a programmable defibrillation pulse generator, this lead system allows the physician to determine an optimal defibrillation regime for the particular patient in which it is implanted.

Figure 6B:
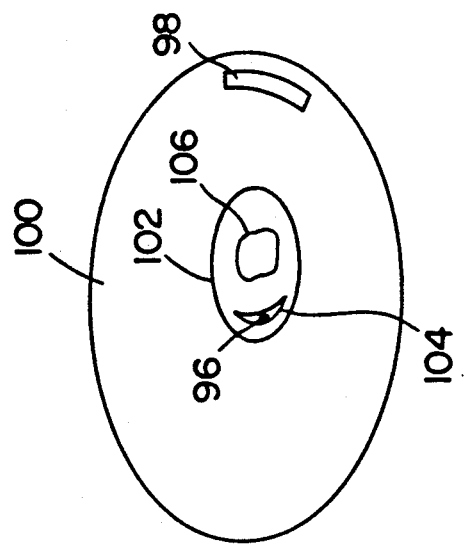
FIGS. 6A and 6B show an alternative embodiment of a defibrillation lead system employing the lead of FIG. 1 in conjunction with a subcutaneous plate electrode.
Figure 6A:
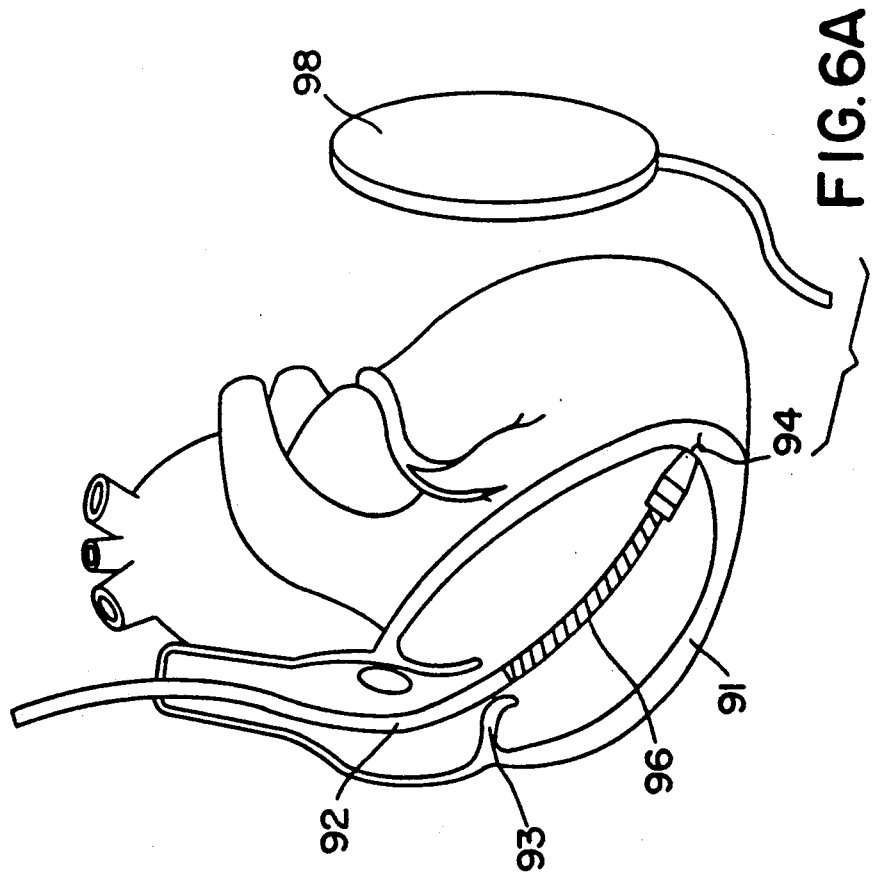

FIG. 6A illustrates a second defibrillation electrode system, which also avoids the necessity of a thoracotomy. This electrode system employs a ventricular defibrillation lead 92, corresponding to the lead illustrated in FIG. 1. The distal end of the lead is located in the right ventricle, and is secured by means of coil electrode 94. As illustrated, the defibrillation electrode 96 extends to about the region of the tricuspid valve 93. However, electrode 96 may, in some cases, extend into the right atrium. The second electrode in the system is a subcutaneous plate electrode 98, which may be any of the various known subcutaneous plate electrodes. In this embodiment of the system, it is desirable that the subcutaneous electrode be located across the left ventricular cavity from the right ventricular electrode, to insure that a substantial percentage of the left ventricle is between the electrodes. As such, it appears that a lateral, subcutaneous location for electrode 98 is desirable.

FIG. 6B shows a stylized cross-section of the human body in the region of the heart. The thorax 100 is illustrated in outline, with the heart 102 located therein. The right ventricular electrode 96 is shown in cross-section within the right ventricular cavity 104. The subcutaneous electrode 98 is shown mounted in a lateral location, across the left ventricular cavity 106 from the right ventricular electrode 96.

The biphasic defibrillation waveform illustrated in FIG. 4 is also useful in conjunction with an electrode system as illustrated in FIGS. 6A and 6B, and is believed to provide somewhat increased efficiency as compared to a corresponding monophasic capacitive discharge pulse.

Figure 7B:
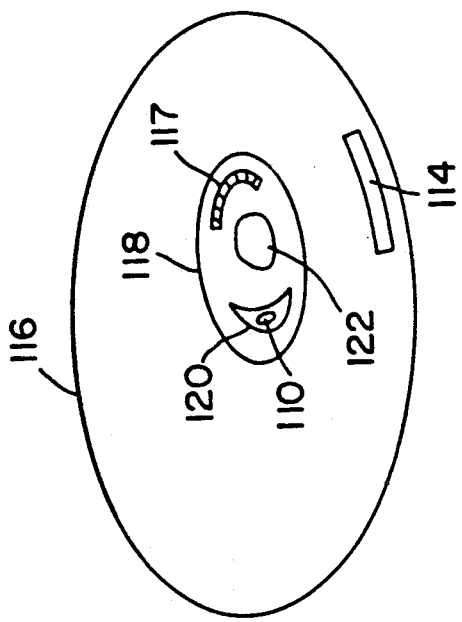
FIGS. 7A and 7B show an additional defibrillation lead system employing the defibrillation leads of FIGS. 1, 2 and 3 in conjunction with a subcutaneous plate electrode.
Figure 7A:
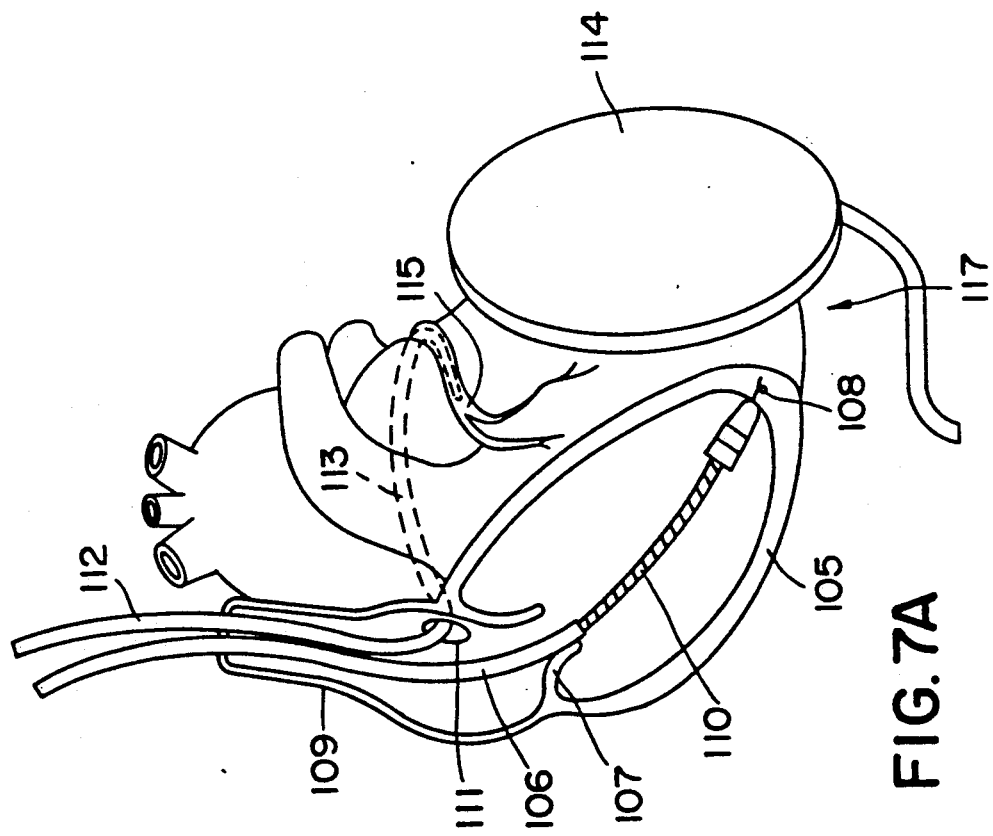

FIG. 7A illustrates a third defibrillation electrode system which may be employed without the necessity of a thoracotomy. This system employs a ventricular defibrillation lead 106, corresponding to the lead illustrated in FIG. 1. The distal end of the lead is located in the right ventricle 105 and is secured by means of coil electrode 108. The defibrillation electrode 110 extends generally to the region of the tricuspid valve 107. The second lead is a coronary sinus lead 112, corresponding to the lead of FIG. 2. Lead 112 passes through the superior vena cava 109, into the opening of the coronary sinus 111 and through the great vein 115. When so mounted, the elongated defibrillation electrode 113 mounted on lead 112 extends from a point within the opening of the coronary sinus 111 and terminates in the great vein 115 roughly adjacent the left atrial appendage. It is important that the proximal ends of electrodes 110 and 113 are not located to closely to one another to prevent excessive current density in the area adjacent thereto. Preferably, the proximal end of electrode 110 terminates within the right ventricle and the proximal end of electrode 113 is 3-5 cm within the opening of the coronary sinus.

The third electrode is a subcutaneous plate electrode 114, which may be any of the various known subcutaneous plate electrodes. In this embodiment, the subcutaneous electrode may be located anteriorly or somewhat laterally on the thorax, generally overlying the ventricular area of the heart.

FIG. 7B shows a stylized cross-section of the human body in the region of the heart. The thorax 116 is illustrated in outline, with the heart 118 located therein. The right ventricular electrode 110 is shown in cross-section within the right ventricular cavity 120. The coronary sinus electrode 113 is shown extending around the base of the heart, in the vicinity of the left ventricular cavity 122. The subcutaneous electrode 114 is shown located subcutaneously over the ventricular portion of the heart. The electrode system illustrated in FIGS. 7A and 7B is useful in conjunction with a variety of defibrillation pulse regimes, including sequential, simultaneous and single pulse regimes.

U.S. Pat. No. 4,727,877, issued to Kallok, discloses a multiple electrode, multiple pulse regime employing electrodes in the superior vena cava, the right ventricle, and the coronary sinus. The defibrillation regime disclosed therein is believed to be effective and to provide a usable defibrillation lead system which does not require a thoracotomy. However, defibrillation electrode systems employing right ventricular, coronary sinus and subcutaneous plate electrodes as illustrated in FIG. 7A are believed to provide for an increase in efficiency over the system illustrated in Kallok.

Multiple pulse defibrillation regimes which may be employed with the electrode system of FIGS. 7A and 7B first pair two of the electrodes, and then pair the third electrode with one of the two electrodes first paired. For example, the first pulse may be delivered between the right ventricle and the subcutaneous plate, and the second pulse delivered between the coronary sinus electrode and subcutaneous plate. Alternative pulse regimes employ the right ventricular electrode sequentially paired with the coronary sinus and subcutaneous plate and the coronary sinus electrode sequentially paired with the right ventricular electrode and the subcutaneous plate. Regardless of which of these three regimes is chosen, there appears to be an improvement in efficiency as compared to an electrode system employing a superior vena cava electrode, a right ventricular electrode and a coronary sinus electrode as described in Kallok. Kallok suggests the substitution of a subcutaneous plate electrode for the coronary sinus electrode, and the Tacker et al patent cited above also discloses such a system. It is believed that the electrode system of FIGS. 7A and B will also provide improved efficiency as compared to such electrode systems.

One of the advantages of the electrode system of FIGS. 7A and 7B is its flexibility. This electrode system is capable of providing a variety of effective defibrillation pulse regimes. For example, the electrode system of FIGS. 7A and 7B may be employed to deliver a multielectrode simultaneous pulse defibrillation regime which may be beneficial in some patients. In the simultaneous pulse regimes, two of the three electrodes are tied together, and a pulse is delivered between the two tied electrodes and the third electrode. Tests were performed in which the coronary sinus and subcutaneous plate electrode were paired, in which the subcutaneous plate and right ventricular electrode were paired, and in which the subcutaneous plate and coronary sinus electrode were paired. All three pulse regimes provided efficient defibrillation. The multiple electrode simultaneous pulse system which appeared to have provided the greatest increase in efficiency was the system in which right ventricular and coronary sinus electrode were paired, and a pulse applied between them and the subcutaneous plate.

In the multiple electrode simultaneous pulse regimes discussed above, it appears that use of the biphasic, asymmetric waveform described in FIG. 4 is also of some advantage. It is believed that the asymmetric biphasic pulse provides some increase in efficiency as compared to a single pulse regime employing a corresponding monophasic capacitive discharge waveform.

The lead system of FIG. 7 may also be used to provide two electrode, single pulse defibrillation regimes, such as those described in conjunction with FIGS. 5, 6 and 8. In particular, test results suggest that delivery of single pulses between the right ventricular electrode 110 and the coronary sinus electrode 113 is more efficient than delivery of single pulses between electrodes located in the right ventricle and the superior vena cava, as disclosed in the prior art. In this context, use of the biphasic defibrillation pulse illustrated in FIG. 4 is also believed to provide improved efficiency as compared to use of a corresponding monophasic pulse. Because of the large variability from patient to patient, flexibility in an electrode system is believed to be desirable so that the pulse regime may be more easily tailored to fit the particular patient involved.

Figure 8B:
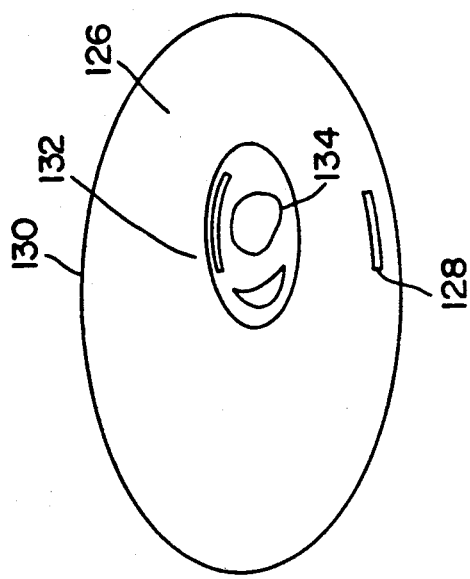
FIGS. 8A and 8B show a defibrillation lead system employing the electrodes of FIGS. 2 and 3 in conjunction with a subcutaneous plate electrode.
Figure 8A:
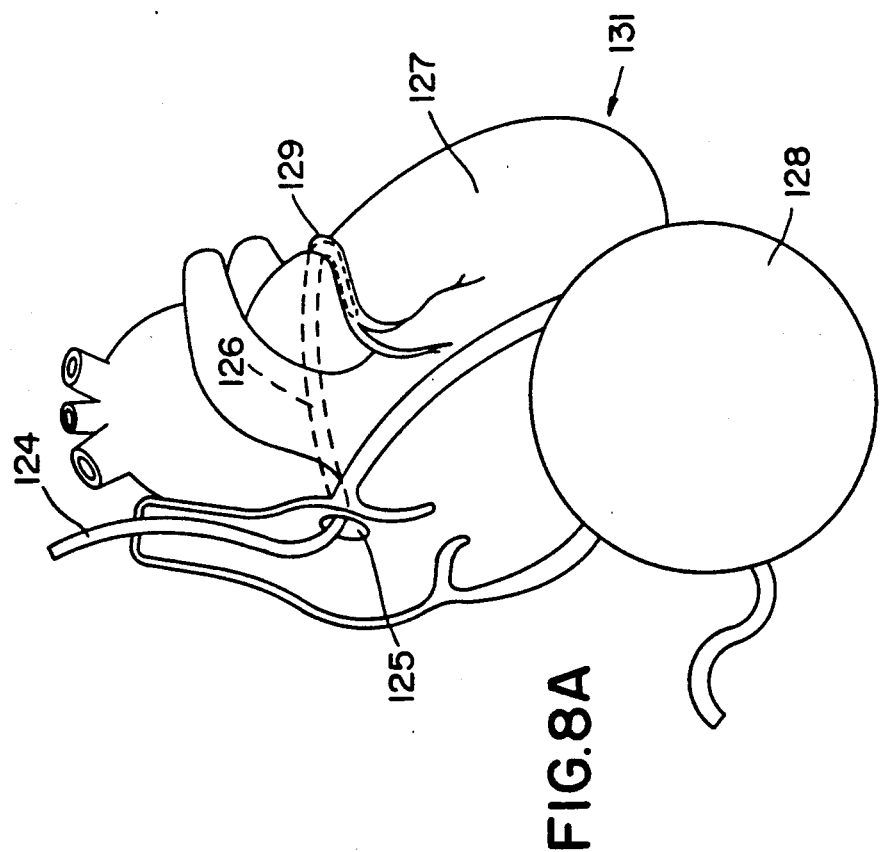

FIG. 8A shows a fourth defibrillation electrode system which avoids the necessity of a thoracotomy. This system employs a coronary sinus electrode 124 corresponding to the lead of FIG. 2. The electrode 126 extends from the opening into the coronary sinus 125, around the base of the heart and terminates in the great vein 129. In this electrode system, it is not necessary that the proximal end of electrode 126 be located within the coronary sinus. It may extend into the atrium. Moreover, it is not necessary that the distal end of electrode 126 extend all the way to the vicinity of the left atrial appendage. The second electrode 128 is a subcutaneous patch electrode. In this electrode system, single monophasic or biphasic defibrillation pulses are applied between electrode 126 and electrode 128.

FIG. 8B shows a stylized cross-section through the human body in the vicinity of the heart. The thorax 130 is illustrated in outline, with the heart 132 located therein. In this view, the electrode 126 of the coronary sinus can be seen extending from the atrium, around the left base of the left ventricle 134, terminating in the great vein. Subcutaneous plate electrode 128 is shown located anteriorally, subcutaneously, in the vicinity of the apex of the heart.

The electrode system illustrated in FIGS. 8A and 8B appears to provide an improvement in efficency over prior art electrode systems employing single pulse regimes delivered between superior vena cava and right ventricular electrodes, as disclosed in the Mirowski patents cited above. In addition, this electrode system also appears to provide some improvement in efficiency over the coronary sinus/right ventricular electrode system illustrated in FIG. 5A. However, it does not have the convenience of being a totally endocardial electrode system. In conjunction with the electrode system of FIGS. 8A and 8B, the asymmetric, biphasic pulse waveform illustrated in FIG. 4 is believed to provide some increase in efficiency as compared to a similar monophasic capacitive discharge pulse.

In conjunction with the above specification, I claim:

1. A method of defibrillating a patient's heart, comprising the steps of:

transvenously inserting an elongated first electrode into the right ventricle of said patient's heart such that said first electrode extends from approximately the apex of the right ventricle to the tricuspid valve of said heart, said first electrode contained entirely within the right ventricle of said patient's heart;

transvenously inserting a second electrode into the coronary sinus and great vein of said patient's heart, said second electrode extending from a first point within the coronary sinus to a second point adjacent the left atrial appendage of said patient's heart;

subcutaneously inserting a third electrode at the level of said patient's heart; and applying a defibrillation pulse between said second electrode and one of said first and third electrodes and subsequently applying a defibrillation pulse between said second electrode and the other of said first and third electrodes.

2. A method of defibrillating a patient's heart, comprising the steps of:

transvenously inserting a first electrode into the right ventricle of said patient's heart;

transvenously inserting a second electrode into the coronary sinus and great vein of said patient's heart;

subcutaneously inserting a third electrode at the level of said patient's heart; and sequentially applying defibrillation pulses between said first and second electrodes and between said second and third electrodes.

3. A method of defibrillating a patient's heart, comprising the steps of:

inserting a first elongated electrode into the coronary sinus and great vein of said patient's heart;

subcutaneously inserting a second electrode at the level of said patient's heart; and applying a defibrillation pulse between said first and second electrodes.

* * * * *